United States Patent [19]
Cordes et al.

[11] Patent Number: 6,153,216
[45] Date of Patent: Nov. 28, 2000

[54] TRANSDERMAL ESTRADIOL/ PROGESTOGEN AGENT PATCH AND ITS PRODUCTION

[75] Inventors: Günter Cordes, Lagenfeld, Germany; Antonino Santoro; Ivo Setnikar, both of Monza, Italy

[73] Assignee: Rotta Research B.V., Amsterdam, Netherlands

[21] Appl. No.: 09/091,395

[22] PCT Filed: Dec. 20, 1996

[86] PCT No.: PCT/EP96/05759

§ 371 Date: Sep. 14, 1998

§ 102(e) Date: Sep. 14, 1998

[87] PCT Pub. No.: WO97/23227

PCT Pub. Date: Jul. 3, 1997

[30] Foreign Application Priority Data

Dec. 22, 1995 [DE] Germany ............ 195 48 332

[51] Int. Cl.[7] ...................................... A61F 13/00
[52] U.S. Cl. ................ 424/449; 424/448; 514/691; 514/731; 602/41; 602/60; 604/892.1; 604/307
[58] Field of Search ............... 424/448, 449; 514/731, 691; 682/41, 60; 604/892.1, 307

[56] References Cited

U.S. PATENT DOCUMENTS

| 4,913,905 | 4/1990 | Fankhauser et al. | 424/449 |
| 5,032,403 | 7/1991 | Sinnreich | 424/448 |
| 5,128,124 | 7/1992 | Fankhauser et al. | 424/449 |
| 5,198,223 | 3/1993 | Gale et al. | 424/449 |
| 5,225,199 | 7/1993 | Hidaka et al. | 424/443 |
| 5,252,334 | 10/1993 | Chiang et al. | 424/443 |
| 5,393,529 | 2/1995 | Hoffmann et al. | 424/445 |
| 5,422,119 | 6/1995 | Casper | 424/449 |
| 5,683,711 | 11/1997 | Fischer et al. | 424/449 |
| 5,711,962 | 1/1998 | Cordes et al. | 424/447 |
| 5,830,505 | 11/1998 | Fischer et al. | 424/487 |

FOREIGN PATENT DOCUMENTS

| 0156080B2 | 12/1984 | European Pat. Off. . |
| 0285563A1 | 5/1988 | European Pat. Off. . |
| 0356382A2 | 2/1990 | European Pat. Off. . |
| 0416842B1 | 3/1990 | European Pat. Off. . |
| 0416842A1 | 3/1991 | European Pat. Off. . |
| 3810896A1 | 3/1988 | Germany . |
| 3933460A1 | 10/1989 | Germany . |
| 4308406C1 | 6/1994 | Germany . |
| WO9011064 | 10/1990 | WIPO . |
| WO920581 | 4/1992 | WIPO . |
| 9423707 | 10/1994 | WIPO . |
| 9509618 | 4/1995 | WIPO . |
| 9603119A1 | 2/1996 | WIPO . |

OTHER PUBLICATIONS

Derwent WPI Abstract for DE 4308406C1 (Abstract Date, 1994).

International Search Report for Application PCT/EP96/05759.

Explanation concerning the contents of German Patent DE 4308406 concerning U.S. Application: Transdermal Estradiol/Progestogen Agent Patch and its Production by Günter Cordes et al., Application No. 09/091,395.

Primary Examiner—S. Mark Clardy
Assistant Examiner—Michael A. Williamson
Attorney, Agent, or Firm—Volpe and Koenig, P.C.

[57] ABSTRACT

The invention concerns a transdermal patch for the release through the skin of estradiol and a progestogen agent and a process for its production.

23 Claims, No Drawings

TRANSDERMAL ESTRADIOL/PROGESTOGEN AGENT PATCH AND ITS PRODUCTION

This application is a 371 of PCT/EP96/05759 filed Dec. 20, 1996.

INTRODUCTION

The invention regards a transdermal patch delivering estradiol and a progestogen for the hormone replacement therapy.

BACKGROUND INFORMATION

At an average age between 45 and 52 years, in the women there is a gradual decline of the ovarian function ending with the cessation of ovulation and of the endocrine secretion of sexual hormones. This condition is called menopause and is connected with a number of unpleasant symptoms, such as hot flushes, sweats, insomnia, vaginal dryness and depression. In the long term the estrogen deficiency leads to a generalized atrophy of the skin, loss of hairs, urogenital atrophy and dysfunction, accelerated bone loss from the skeleton producing osteoporosis and rapid increase of the incidence of coronary heart diseases. All these adverse sequelae can be reversed by an appropriate replacement therapy with estrogen agents, i.e. by the "Hormone Replacement Therapy__(HRT).

Several types of estrogens are used for the HRT, e.g. conjugated equine estrogens, estradiol, estrone, etc., with a preference for estradiol which is the most potent physiological estrogen hormone.

Estradiol can be administered by parenteral or oral route. The oral administration has several problems, because estradiol is almost insoluble in water and its bioavailability is scarce and largely depending on the galenical formulation and physical properties of the active substance. Therefore the bioavailability is very variable even in the same subject. In addition, estradiol undergoes to a intense first pass effect in the intestine and in the liver, with the formation of several metabolites. These metabolites greatly loss the estrogen potency but maintain some adverse effects, including the increase of risk of cancer. In addition the oral administration provokes very large and unphysiological fluctuations of the hormonal blood levels and exposes the subjects to an unnecessary load of estrogen substances.

The ideal administration route, because closest to the physiological secretion of estradiol, would be the intravenous slow infusion. This administration is evidently not practicable. Similar pharmacokinetic pattern as with intravenous slow infusion can be obtained by transdermal administration, because by this route the liver is bypassed and estradiol is directly supplied to the circulation. Furthermore the transdermal release of estradiol is rather constant, similar to that occurring physiologically from the ovary, without the daily large fluctuations which characterize the oral administration.

The most convenient dosage form for the transdermal administration is the "Transdermal Patch__, i.e., according to the European Pharmacopoea, "flexible pharmaceutical preparations of various sizes, containing one or more active ingredients. They are intended to be applied on the unbroken skin in order to deliver the active ingredient(s) to the systemic circulation after passing through the skin barrier__.

Different types of transdermal patches were developed. The first used for estradiol is a liquid reservoir patch (U.S. Pat. No. 4,379,454) which contains estradiol in an alcoholic gel solution. The diffusion of estradiol to the skin is controlled by a rate limiting membrane. This type of patch needs the presence of a solubilizer of estradiol which has also the function of absorption enhancer and is represented by ethanol. From this type of patches estradiol is released rapidly in the first 1–2 days, and then more slowly. Therefore the estradiol concentrations in blood during a 3–4 day application of this patch are not constant. Furthermore the presence of alcohol produces skin irritation in a certain number of patients. For these reasons the liquid reservoir type patches are more and more replaced by the solid matrix patches of the new generation, in which estradiol is incorporated into the adhesive matrix which adheres directly to the skin.

In women with intact uterus the estradiol replacement therapy often produces hypertrophy of the endometrium which may lead to endometrial cancer. To prevent this risk the estrogen therapy in women with intact uterus must be intermittently "opposed by the administration of a progestogen agents, to provoke a menstruation-like cleavage and renewal of the endometrial mucosa. In general the progestogen opposition is obtained administering by oral route for 10–14 days a progestogen, such as progesterone, medroxyprogesterone acetate, dydrogesterorie, norethisterone, etc.

Obviously a transdermal patch containing estradiol and progestogen would be more practical than the transdermal estrogen administration combined with the oral progestogen administration. The inclusion of the progestogen in an transdermal patch, however, faces several obstacles, first of all the relatively high doses of the progestogen needed to have an efficient opposition. In most cases these high doses cannot be vehicled in a transdermal patch. Further obstacles are the instability and the scarce solubility of most progestogens.

DESCRIPTION OF THE INVENTION

The present invention describes a transdermal patch delivering estradiol and a progestogen in doses suitable for an effective HRT. The transdermal patch is formed by a backing foil, impermeable to the active ingredients and to the adhesive of the matrix, by a layer of adhesive matrix which contains estradiol and the progestogen, and by a release liner, to be removed immediately before the application of the patch on the skin. Absorption enhancers were avoided, in order to assure a good tolerability by the skin. Nevertheless, surprisingly, a good transdermal release of estradiol and of the progestogen was obtained due to the physical status of the active ingredients in the specially formulated adhesive matrix.

The solid matrix type patch has a simple structure and is relatively easy to produce. However its development needs several inventive steps in order to solve different problems. Some problems are related to the active ingredients, e.g. chemical instability and crystallisation. Other problems are related to the adhesive matrix which must comply with several requirements, such as having good tacking properties in order to adhere to the skin by light pressure, a good intrinsic cohesion in order to avoid a creeping from the patch, it must allow an easy removal from the skin and, upon removal, it must stick to the backing foil and not leave residues on the skin.

These prerequisites were achieved in the present invention.

This invention regards a transdermal patch for the hormone replacement therapy in women, and particularly a transdermal patch releasing estradiol as estrogen agent and norethisterone acetate (NETA) as progestogen agent.

Among the different progestogens, NETA was selected:
a) because it is effective at low doses and therefore suitable to be formulated in a transdermal patch which can vehicle only limited amounts of active ingredients;
b) because NETA, being a nor-androsterone derivative, has some additional effects, e.g. on libido, that are absent in pregnene derivatives as progesterone or medroxyprogesterone.

Objective of the present invention was the achievement of a transdermal patch which could release rather constant amounts of estradiol and NETA during its whole possible application time, i.e. from 3 to 7 days.

A second objective was to achieve a transdermal patch with a very simple structure. For this purpose a "monolytic__" type matrix patch was developed, in which the matrix is both the pressure sensitive adhesive and the reservoir of the active ingredients.

A third objective was to achieve the transdermal patch with a good skin compatibility and therefore without absorption enhancers.

A fourth objective was to formulate the adhesive base with optimum tacking, adhesion and cohesion properties, in order to accomplish an easy application onto the skin, and an easy and complete removal of the patch from the skin at the end of the scheduled application period. In addition the cohesion of the matrix had to be adequate to avoid creeping of the adhesive matter during storage.

Surprisingly it was found that these complex objectives could be achieved by a transdermal patch composed by two layers: a drug-free backing layer and a layer of optimally cross-linked acrylic adhesive containing also the active ingredients.

To protect the adhesive matrix during storage a release liner was applied on the matrix, that must be removed immediately before application of the patch on the skin.

The backing layer or foil according to the present invention can be any occlusive material with a thickness of 10 to 50 μm (preferably 13 to 25 μm), such as polyurethane, polyethylene, polypropylene, polyvinylchloride or, preferably, polyester materials. It must be impermeable to the active ingredients and to the components to the adhesive matrix. Furthermore the adhesion of the backing foil with the matrix must be such that upon removal of the patch the adhesive matrix remains stuck on the backing foil without leaving residues on the skin. For this purpose the backing foil may be lacquered on the matrix side. A suitable lacquer among others may be composed by epoxy resin, polyaminoamide resin and precipitated calcium carbonate.

The pressure sensitive adhesive matrix was chosen from a group of vinylacetate containing acrylate copolymers.

Since the matrix was also the drug reservoir of the transdermal patch, several inventive steps were needed to find a composition in which estradiol and NETA were in a physical state favouring the diffusion to and through the skin, without the aid of an absorption enhances. Absorption enhancers were deliberately avoided in the formulation of the matrix because they act by increasing the permeability of the stratum corneum of the skin through a disruption of the cellular layer and therefore through a lesion of the skin. In addition absorption enhancers are also absorbed through the skin and may have systemic adverse effects. Finally in the presence of absorption enhancers, the absorption of the active ingredients is linked to the concentration of the absorption enhancer, that varies in time due to the absorption of the enhancer itself and causes an inconstant absorption of the active ingredients.

The following were the monomers in the vinylacetate acrylate copolymer.
a) 2-Ethylhexyl acrylate (2-EHA) in a concentration between 50% and 85%, preferably between 61% and 75% and especially 65 to 71%.
b) Hydroxyethyl acrylate (HEA) in a concentration between 3.5% and 6.5%, preferably between 4.5% and 5.5%.
c) Vinylacetate (VA) in a concentration between 16% and 35%, preferably between 24% and 28%.
d) Glycidylmethacrylate (GMA) up to a concentration of 0.3%, preferably between 0.1% and 0.2%. These small quantities of GMA surprisingly improved the cohesion of the copolymer, thus minimizing creeping.

The cohesion-adhesion properties of the copolymer matrix were improved by adding a cross-linker, i.e. aluminum acetyl acetonate (AlAc), in a concentration in the final matrix between 0.4% and 0.7%, preferably between 0.5% and 0.6%.

In this complex adhesive matrix, estradiol and NETA could be incorporated in surprisingly high concentrations, e.g. estradiol between 0.6% and 1.8%, preferably between 1.0% and 1.4% and especially 1.2 to 1.4%, and NETA between 4.0 and 10.0%, preferably between 7.0 to 9.5%, especially 7.0% and 9.0% and preferably 8.0 to 9.0%. In these concentrations estradiol and NETA are in supersaturated solid solution in the copolymeric matrix, a condition which confers to the active ingredients the thermodynamic activity required for a forced diffusion through the skin even in the absence of an absorption enhancers.

This base of the adhesive matrix, however, has problems with the stability of the active ingredients. In fact stability tests have shown that with this formulation the active components tended to form crystals during storage. Surprisingly it was found that the addition of small amounts of octyldodecanol, i.e. between 1.3% and 3.5% and especially 1.3 to 3.2%, (preferably between 1.8% and 2.7% and especially 2.0 to 2.5%), could prevent the crystallisation from the supersaturated solution of active ingredients, even after prolonged storage.

Another problem which was not previously described and/or solved is the chemical instability of NETA during storage, even at room temperature, with the formation of up to 5% of degradation products per year. Surprisingly it was found that the chemical instability of NETA could be prevented by excluding humidity from the matrix. This was achieved e.g. by manufacturing the patch under a flux of dry air. The stability of NETA could also be improved by the inclusion in the final container of the patch, i.e. in the sachet, a suitable desiccant agent, such as silica gel, sodium sulfate or calcium sulfate. Finally it was surprisingly found that the stability of NETA could be improved by dissolving estradiol and NETA during the manufacturing process in a mixture of methylethylketone/ethanol, in a proportion (w/w) between 2:1 and 4:1, preferably between 2.5:1 and 3.5:1.

The release liner used to protect the matrix during storage must be impermeable to the active ingredients and to the pressure sensitive adhesive, and must be easy to detach from the matrix of the patch before use, without removing any amount of the medicated matrix. For the present invention several types of siliconized sheets of material were found suitable, e.g. polyethylene, paper, polyvinylchloride, polypropylene or polyester, or a combination of these materials. The optimum thickness of the release liner was between 80–300 $\mu$m and preferably 80–200 $\mu$m. To be easily removable, the release liner must have an appropriate rigidity. A pull-off tag was cut in the release liner to facilitate its detachment from the patch.

From the composite medicated foil pieces of circular or oval or of other shape were punched, of an area between 20 and 100 $cm^2$, according to the required release rate of active ingredients.

The obtained complete patches were individually sealed in containers represented by sachets of humidity-impermeable materials, e.g. composite foils of aluminum, paper, polyethylene or polyvinylchloride, coated in the internal surface by an appropriate coating material to prevent sticking of the patch on the wall of the sachets.

In order to maintain a dry environment (to prevent the degradation of NETA) the sealing of the sachets had to be performed in an environment with low humidity.

As a further precaution a desiccant, e.g. silica gel, sodium sulfate, or calcium sulfate, may be included in the sachets, with adequate precautions to prevent the contamination of the patch with the desiccant.

EXAMPLES

The manufacture of transdermal patches delivering estradiol and NETA prepared according to the present invention is illustrated by the following examples.

Example 1

Reference Manufacturing Procedure
Adhesive Mixture with Active Ingredients

1. The adhesive mixture is prepared dissolving in 8.4 kg ethyl acetate a copolymer obtained by radical polymerization of 5712 g 2-ethylhexyl acrylate, 2184 g vinyl acetate, 420 g 2-hydroxyethyl acrylate and 12.6 glycidylmethacrylate.

2. Quantities of 125 g estradiol, 832.5 g NETA, 216.3 g octyldodecanol and 52.5 aluminum acetylacetonate are dissolved or finely suspended in 4.75 kg methylethylketone. This solution is added under stirring to the solution of copolymer, prepared as described above.

3. The mixture is stirred until a homogeneous mass is obtained. Acetic acid ethylester and methylketone (63:27 w/w) is added to obtain a solid content of 42.3%.

Preparation of the Composite Medicated Foil

4. The adhesive mixture containing the active ingredients is spread onto a foil of silicone-coated paper or silicone-coated polyester and dried at a temperature between 35° and 85° C. to produce a film of matrix weighing 96±5% $g/m^2$ as dry weight and corresponding to 1.25 g estradiol and 8.32 g NETA per $m^2$ of the dry matrix. The evaporation may be accelerated by vacuum.

5. Finally the backing foil, i.e. a polyester foil 17 to 25 $\mu$m thick, lacquered on the matrix site with a lacquer consisting of epoxy resin, polyaminoamide resin and precipitated calcium carbonate, is stuck on the matrix to form the composite medicated foil for the transdermal patch.

Punching of the Transdermal Patches

6. Circular or oval or of other shapes patches having an area of 40 $cm^2$, each containing 5±0.5 mg estradiol and 33±3.3 mg NETA are punched from the composite medicated foil to form the final transdermal patches. Patches with other areas, e.g. from 20 to 100 $cm^2$, can be punched, according to the release rate of estradiol and of NETA required for the patch.

Sealing into the Final Container

7. The patches are individually sealed into sachets of a water and humidity impermeable multilayered foil, e.g. composed by sheets of Surlyn$^r$, aluminum, polyethylene and paper.

Example 2

Manufacture Using an Intermediate Liner
Adhesive Mixture with Active Ingredients
Proceed as in steps 1–3 of Example 1.
Preparation of the Composite Medicated Foil 4. The adhesive mixture containing the active ingredients is spread onto a foil of silicone-coated paper or silicone-coated polyester, and dried at a temperature between 35° and 85° C. to produce a film of matrix weighing 96±5% $g/m^2$ as dry weight and corresponding to 1.25 g estradiol and 8.32 g NETA per $m^2$ of the dry matrix. This is the intermediate liner needed for the production of the transdermal patch.

5. A silicone-coated paper or silicone-coated polyester, 50–200 $\mu$m thick, is stuck on the matrix and the intermediate liner is detached. In the same process the backing foil, i.e. a lacquered polyester foil 15–25 $\mu$m thick, is stuck on matrix to form the composite medicated foil for the transdermal patch.

Punching of Patches

6. Circular or oval patches having an area of 40 $cm^2$, each containing 5±0.5 mg estradiol and 33±3.3 mg NETA are punched from the composite medicated foil to form the final transdermal patch. Other patch areas can be punched, according to the requested delivery rate of estradiol and NETA.

Sealing into the Final Container
Proceed as in step 7 of Example 1.

Example 3

Manufacture Under Dry Air
Adhesive Mixture with Active Ingredients
Proceed as in steps 1–3 of Example 1.
Preparation of the Composite Medicated Foil 4. The adhesive mixture containing the active ingredients is spread onto a foil of silicone-coated paper or silicone-coated polyester. The solvents are evaporated under a flux of dry air heated at a temperature between 60° and 90° C.

5. The backing foil, i.e. a polyester foil 17 to 25 μm thick, is stuck directly on the matrix as soon as the evaporation of the solvents is completed. By this process the matrix does not come into contact with the environmental air, which may contains a notable degree of humidity and provoke chemical instability of NETA.

Punching of Patches

Proceed as in step 6 of Example 1.

Sealing into the Final Container

Proceed as in step 7 of Example 1.

Example 4

Dissolution of Active Ingredients in a Methylethylketone/Ethanol Mixture

Adhesive Mixture with Active Ingredients

1. An adhesive mixture is prepared dissolving in 8.4 kg ethyl acetate a copolymer obtained by radical polymerization of 5712 g 2-ethylhexyl acrylate, 2184 g vinyl acetate, 420 g 2-hydroxyethyl acrylate and 12.6 glycidylmethacrylate.

2. Quantities of 125 g estradiol, 832.5 g NETA, 216.3 g octyldodecanol and 52.5 aluminum acetylacetonate are dissolved or finely suspended in 4.75 kg of a mixture of methylethylketone and ethanol (from 2:1 to 4:1 w/w). This solution is added under stirring to the solution of copolymer, prepared as described above.

3. The mixture is stirred until a homogeneous mass is obtained. Acetic acid ethylester and methylethylketone (63:27 w/w) is added to obtain a solid content of 42.3%.

Preparation of the Composite Medicated Foil

Proceed as in steps 4 and 5 of Example 1, or of Example 2, or preferably, of Example 3.

Punching of the Transdermal Patches

Proceed as in step 6 of Example 1.

Sealing into the Final Container

Proceed as in step 7 of Example 1.

Example 5

Sealing into Sachets with Desiccant

Adhesive Mixture with Active Ingredients

Preparation of the Composite Medicated Foil

Punching of Patches

Proceed as in steps 1–6 of Example 1–4 or, preferably, of Example 5.

Sealing into the Final Containers

7. The patches are individually sealed into sachets of a humidity-impermeable multilayered foil with the composition described in Example 1. In the sachet also a desiccant is sealed, e.g. silica gel, sodium sulfate, calcium sulfate or other desiccants, with provisions that avoid the contamination of the transdermal patch with the desiccant.

What is claimed is:

1. A transdermal patch for the release through the skin of estradiol and norethisterone acetate (NETA), consisting of an outer backing layers a matrix and a protective release liner, wherein the backing layer is impermeable to the drugs and supports the matrix, the matrix being a crosslinked pressure-sensitive adhesive copolymer matrix in which the active ingredients are dissolved or dispersed and wherein the matrix is covered by the protective release liner impermeable to the drugs that must be removed immediately before the application of the patch onto the skin, wherein said crosslinked pressure sensitive adhesive copolymer matrix is obtained by radical copolymerization of between 50 to 85% 2-ethylhexyl acrylate, 3.5 to 6.5% hydroxyethyl acrylate, 16 to 35% vinylacetate and up to 0.3% glycidyl methacrylate and, optionally, in the presence of substances including a cross-linking agent and a crystallization preventative, suitable to improve the stability and/or performance of the patch, and wherein estradiol and NETA are present in a supersaturated solid solution.

2. A transdermal patch according to claim 1, characterized in that the backing layer includes a foil of a material impermeable to the active ingredients and to the adhesive copolymer matrix said material selected from the group consisting of polyester, polyurethane, polyethylene, polypropylene and polyvinylchloride materials; and/or the matrix-facing surface of the backing layer is lacquered, consisting of epoxy resin, polyaminoamido resins and precipitated calcium carbonate; and the backing layer has a thickness between 10 to 50 μm.

3. A transdermal patch according to claim 1, characterized by said crosslinked pressure-sensitive adhesive matrix obtained by radical copolymerization of 2-ethylhexyl acrylate in a concentration of between 61 to 75%, hydroxyethyl acrylate in a concentration of between 4.5 to 5.5%, vinylacetate in a concentration of between 24 to 28%, and glycidyl methacrylate up to a concentration of 0.1 to 0.2%, calculated as w/w based on the matrix.

4. A transdermal patch according to claim 1, characterized by said cross-linking substances being aluminum acetylacetonate, in quantities of between 0.4 to 0.7%.

5. A transdermal patch according to claim 1, characterized by said crystallization preventative being octyldodecanol, in quantities of between 1.3 to 3.5%.

6. A transdermal patch according to claim 1, characterized by a content of estradiol of between 0.6 to 1.8% (w/w in the adhesive matrix).

7. A transdermal patch according to claim 1, characterized by a content of norethisterone of between 4.0 to 10.0% (w/w in the matrix).

8. A transdermal patch according to claim 1, characterized by a content of other substances up to a concentration in the matrix of 2% suitable to improve the stability and/or the performance of the transdermal patch.

9. A transdermal patch according to claim 1, characterized in that the protective release liner is impermeable to the drugs and is made of a foil of paper, polyester, polyethylene, polypropylene or polyvinylchloride; and having a thickness of 80 to 300 μm.

10. A transdermal patch according to claim 9, wherein the foil is coated with silicone on one or both sides.

11. A transdermal patch according to claim 1, characterized by a circular or an oval shape, and/or a surface of 20 to 300 cm$^2$ according to the required release rate of the active ingredients.

12. A transdermal patch according to claim 1, characterized in that it is sealed in a sachet made of a humidity impermeable multi-layered foil, and made of sheets of aluminum, paper, polyethylene or polyvinylchloride.

13. A transdermal patch according to claim 12, wherein the humidity impermeable multi-layered foil is made of a sheet of Surlyn® material.

14. A transdermal patch according to claim 12, characterized in that it is sealed in a sachet together with a desiccant.

15. A transdermal patch according to claim 14, wherein the desiccant is silica gel, sodium sulfate or calcium sulfate.

16. A process for the production of a transdermal patch characterized by the following measures:

a solution of the crosslinked pressure-sensitive copolymer matrix and of estradiol and norethisterone acetate (NETA) as active ingredients is spread onto a foil that shall become the release liner, and the solvents are evaporated, at a temperature of from 35 to 90° C., at atmospheric pressure or under reduced pressure and then covered by a foil which shall become the backing layer; or the solution of the crosslinked pressure-sensitive copolymer matrix and of estradiol and the progestogen agent as active ingredients is spread on a silicone-coated intermediate liner made of paper or polyester, the solvents are evaporated, at a temperature of from 35 to 90° C., at atmospheric pressure or under reduced pressure, a foil that shall become the protective release liner is stuck on the matrix supported by the intermediate liner, and the matrix is transferred from the intermediate liner to the release liner and a foil that shall become the backing layer is stuck on the matrix supported by the release liner; or the solution of the crosslinked pressure-sensitive copolymer matrix and of estradiol and the progestogen agent as active ingredients is spread onto a foil that shall become the backing layer, and the solvents are evaporated, at a temperature of from 35 to 90° C., at atmospheric pressure or under reduced pressure and the release liner is stuck on the matrix supported by the backing layer.

17. A process according to claim 16, characterized in that the solvent is evaporated under dry air, at a temperature of from 35 to 90° C.

18. A process according to claim 16, characterized in that the process is carried out under a flux of dry air.

19. A process according to claim 16, characterized by the following measures:

estradiol and norethisterone acetate (NETA) as active ingredients, octyldodecanol and the cross-linking substance, aluminum acetylacetonate, are dissolved or dispersed in methylethylketone or in a methylethylketone/ethanol mixture in proportions of from 2:1 to 4:1 (w/w);

the resulting solution or suspension is mixed, under stirring, with a solution or suspension of the crosslinked pressure-sensitive adhesive copolymers in ethylacetate; and the resulting mixture is spread onto a foil according to claim 16.

20. A process according to claim 16, characterized in that the resulting patch is sealed into a sachet of a multi-layered humidity impermeable foil, made of a sheet of aluminum, paper, polyethylene or polyvinylchloride.

21. A process according to claim 20, characterized in that the patch is sealed in a sachet together with a desiccant.

22. A process according to claim 20, wherein the multi-layered humidity impermeable foil is made of a sheet of Surlyn® material.

23. A process according to claim 21, wherein the desiccant is silica gel, sodium sulfate or calcium sulfate.

* * * * *